US010077219B2

(12) United States Patent
Puett et al.

(10) Patent No.: US 10,077,219 B2
(45) Date of Patent: *Sep. 18, 2018

(54) CONTINUOUS MIXING REACTOR AND METHOD OF USE

(71) Applicant: E I DU PONT DE NEMOURS AND COMPANY, Wilmington, DE (US)

(72) Inventors: Mark Coleman Puett, Olathe, KS (US); Minye Liu, Wilmington, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/402,304

(22) Filed: Jan. 10, 2017

(65) Prior Publication Data

US 2017/0129826 A1    May 11, 2017

Related U.S. Application Data

(63) Continuation of application No. 14/262,167, filed on Apr. 25, 2014, now Pat. No. 9,580,366.
(Continued)

(51) Int. Cl.
*B01J 19/00* (2006.01)
*B01J 19/18* (2006.01)
*C07C 2/62* (2006.01)

(52) U.S. Cl.
CPC ............... *C07C 2/62* (2013.01); *B01J 19/18* (2013.01); *B01J 2219/00081* (2013.01); *C07C 2527/054* (2013.01)

(58) Field of Classification Search
CPC .. B01J 19/00; B01J 19/18; B01J 2219/00049; B01J 2219/00051; B01J 2219/00074;
(Continued)

(56) References Cited

U.S. PATENT DOCUMENTS 2,800,307 A    7/1957 Putney
3,759,318 A    9/1973 Putney et al.
(Continued)

FOREIGN PATENT DOCUMENTS

CN    2790575 Y    6/2006
CN    203209043 U    9/2013
CN    103357369 A    10/2013

OTHER PUBLICATIONS

PCT International Search Report and Written Opinion dated Aug. 27, 2014.

*Primary Examiner* — Natasha E Young

(57) ABSTRACT

A continuous mixing reactor has an outer shell having a cylindrical portion with a central section and two opposite conical end sections; a circulation tube within the shell so that an annular passage forms between the shell and the circulation tube; an impeller within and positioned adjacent to one end of the circulation tube; and heat exchange means penetrating the outer shell and extending into the end of the circulation tube opposite the impeller. The outer shell has a hydraulic head forming one end of the shell, a heat exchange medium header at the opposite end of the shell. The circulation tube nearer the heat exchange medium header terminates at or downstream from a tangential plane extending through the shell at the intersection of the central section and the conical end section of the cylindrical portion of shell. The reactor is useful in an alkylation process.

19 Claims, 3 Drawing Sheets

Related U.S. Application Data

(60) Provisional application No. 61/816,373, filed on Apr. 26, 2013.

(58) Field of Classification Search
CPC ... B01J 2219/00078; B01J 2219/00081; C07C 2/00; C07C 2/54–2/58; C07C 2/62; C07C 2527/00; C07C 2527/02; C07C 2527/053; C07C 2527/054

See application file for complete search history.

(56) References Cited

U.S. PATENT DOCUMENTS

| | | |
|---|---|---|
| 3,965,975 A | 6/1976 | Edmundson |
| 4,209,656 A | 6/1980 | Prescott et al. |
| 5,531,266 A | 7/1996 | Ragi et al. |
| 5,624,112 A | 4/1997 | Ragi et al. |
| 5,625,112 A | 4/1997 | Ragi et al. |
| 5,811,625 A | 9/1998 | Ragi et al. |
| 6,863,121 B2 | 3/2005 | Menon et al. |
| 9,580,366 B2 * | 2/2017 | Puett .......................... C07C 2/58 |
| 2010/0243208 A1 | 9/2010 | Kar et al. |

* cited by examiner

CONTINUOUS MIXING REACTOR AND METHOD OF USE

CROSS-REFERENCE TO RELATED APPLICATION

This application is a Continuation of application Ser. No. 14/262,167, now U.S. Pat. No. 9,580,366, filed Apr. 25, 2014 which claims priority of U.S. Patent Application 61/816,373 filed Apr. 26, 2013, the contents of both applications are incorporated herein by reference in their entirety for all purposes.

FIELD OF THE INVENTION

The present invention relates to a continuous mixing reactor and method of use, for example, in an alkylation process.

BACKGROUND OF THE INVENTION

A continuous mixing reactor is a reaction vessel that has a continuous mixer having internal circulation, wherein circulation is provided by an impeller. The reactor is a horizontal pressure vessel having an outer shell, an inner circulation tube, a mixing impeller, and an indirect heat exchange provided by a tube bundle. These reactors are suitable for carrying out chemical reactions under conditions providing intimate contact between reactants, in a single phase or in multiple phases. Continuous mixing reactors are known, and examples can be found as described in U.S. Pat. Nos. 3,759,318 and 3,965,975.

Basic operation of a continuous mixing reactor includes:
1. The continuous mixing reactor shell serves to contain the reaction mixture.
2. The circulation tube serves to establish an internal flow path in the reactor (down the center of the circulation tube and through an annular passage which exists between the circulation tube and the shell).
3. The shell has a hydraulic head, which contains shaft sealing means and any required bearings for the impeller shaft. The hydraulic head also incorporates a reversal zone for flow of fluid from the impeller.
4. The impeller effects mixing and circulation in the reactor. A mixing circulating impeller provides high shear and turbulence to reactants to maximize rate.
5. Indirect heat exchanging means provided as a tube bundle containing a heat exchanging medium for addition or removal of heat absorbed or generated during the reaction. Temperature control is achieved by addition or removal of reaction heat by heat exchange throughout a reaction zone in the reactor. Tube bundles may be of the U-tube type, bayonet tube or others.

The conventional flow path within a continuous mixing reactor, starting from the discharge side of the impeller, is through a reversal area in a hydraulic head, thereafter through an annular passage between the circulation tube and the outer shell, at the end of the circulation tube through a reversal area in the end of the reactor opposite the impeller, and finally through the center of the tube bundle, that is, the central section of the reactor, within the circulation tube back to the impeller. Reactants are normally fed as near as possible to the eye of the impeller so that they are immediately and thoroughly mixed and dispersed into the main body of the reaction mix.

The design of a continuous mixing reactor is to maximize circulation and turbulence of the internal fluids.

An example of a process performed in a continuous mixing reactor is alkylation. In an alkylation process light olefins (such as propylene, butylenes, amylenes) are reacted with an isoparaffin (branched alkane), such as isobutane, in the presence of an acid catalyst such as sulfuric acid, to form an alkylate product. The alkylate product is a mixture of gasoline boiling range branched hydrocarbons, which can be blended with a refinery gasoline pool, to increase the gasoline octane and reduce the vapor pressure.

In an alkylation process, olefin and isoparaffin are combined in a feed, which is injected into a suction side of the impeller inside the circulation tube. The impeller rapidly disperses the feed within the acid catalyst to form an emulsion. The emulsion is circulated by the impeller at high rates within the reactor.

Tube wear has been found in continuous mixing reactors having conventional flow paths at the reversal area in the end of the reactor opposite the impeller. In an alkylation process, wear may be due to corrosivity of acid catalyst, temperature and other factors. Flow distribution in the reversal area creates pressure losses resulting in uneven flow to the center of the bundle.

It is desired to reduce and minimize tube wear of tubes in tube bundle heat exchanging means. For example reduce and minimize wear at the end of the circulation tube in a continuous mixing reactor, to more efficiently use the heat exchange capacity of the tube bundle and to provide better flow distribution in the tube bundle. The continuous mixing reactor and method disclosed herein meets these needs.

SUMMARY OF THE INVENTION

The present disclosure provides a continuous mixing reactor which is a horizontal pressure vessel having
 (a) an outer shell, wherein the outer shell has an interior wall and an exterior wall; one or more inlets for fluids, a hydraulic head (or circulating head) forming one end of the shell, a heat exchange medium header at the opposite end of the shell from the hydraulic head; wherein the shell has a generally cylindrical portion between the hydraulic head and the heat exchange medium header, having a central section and two opposite end sections, the central section having a substantially uniform diameter and each end section is a conical section, and a discharge outlet positioned on a surface of the cylindrical portion; and
 (b) a hollow circulation tube, open at both ends, extending from the hydraulic head to a terminal end opposite of the hydraulic head and nearer to the heat exchange medium header, and positioned axially within the shell and spaced from the interior wall thereof such that an annular passage is formed between the circulation tube and the shell; and
 (c) an impeller received within and positioned adjacent to the end of the circulation tube within the hydraulic head of the shell, wherein the impeller provides for mixing of fluid within the reactor, creating a cyclic flow of fluids through said tube; and
 (d) heat exchange means penetrating the outer shell, wherein the heat exchange means has a tube sheet extending from the head exchange medium header into the open end of the circulation tube opposite of the impeller, wherein the heat exchange means penetrates substantially the length of the central section of the cylindrical portion of the outer shell;
characterized as having (1) the end of the circulation tube nearer to the heat exchange medium header terminate at or downstream from (based on direction of flow of fluid through the impeller through a reversal area in the hydraulic head then through the annular passage between the shell and the circulation tube) a tangential plane extending through the shell at the intersection of the central section and the conical end section of the cylindrical portion of shell; or (2) a flow distribution plate attached to the terminal end of the circulation tube.

The continuous mixing reactor disclosed herein is particularly suitable for use in chemical reactions, such as, for example, an alkylation process, in particular, an acid-catalyst alkylation process.

DETAILED DESCRIPTION

Figure 1:
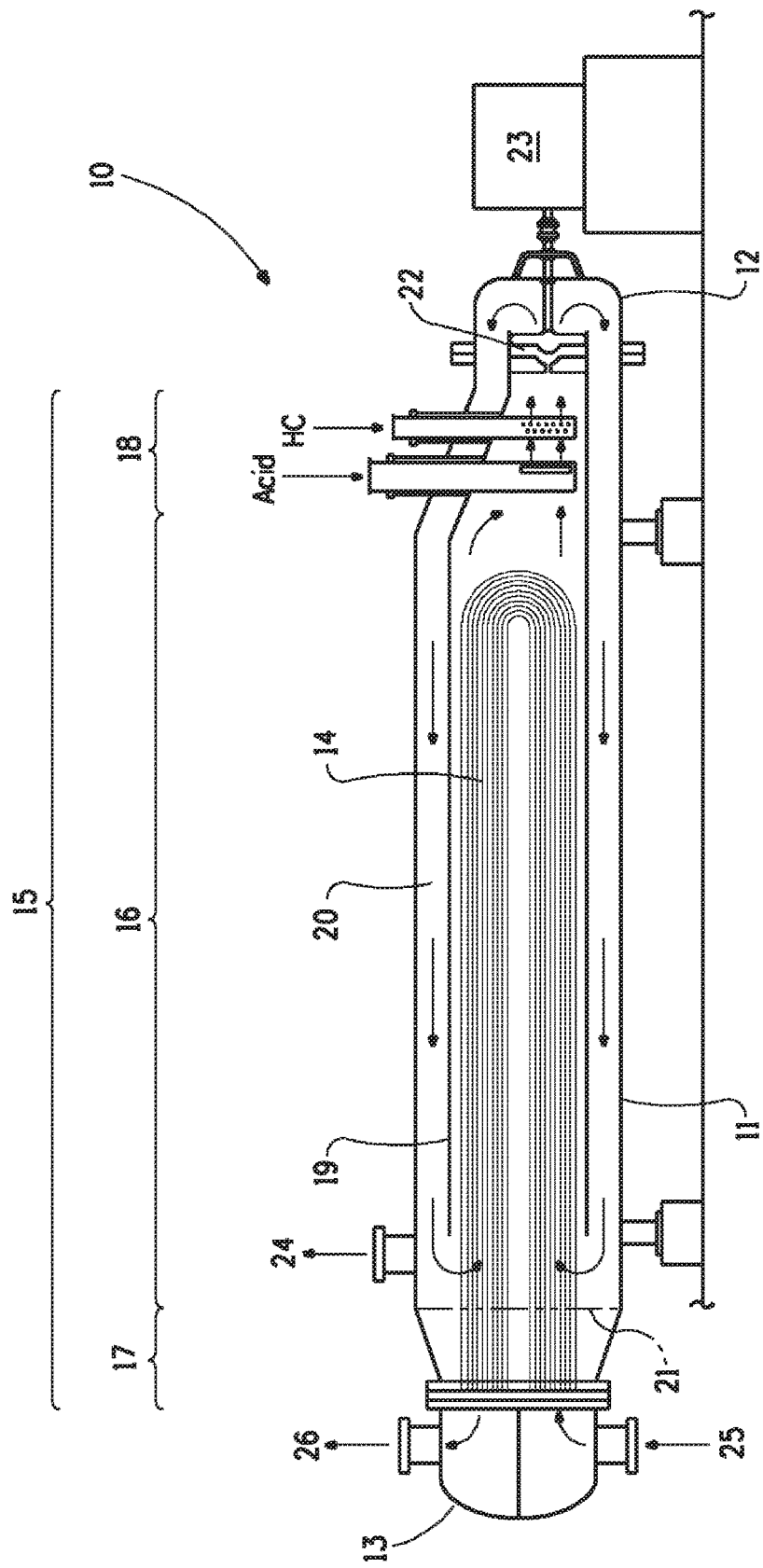
FIG. 1 is a cross-section view of a continuous mixing reactor of the prior art, having a large, elongated U-section heat exchanging tube bundle penetrating the end of the circulation tube opposite the impeller and extending substantially the entire length thereof.

The continuous mixing reactor disclosed herein is a generally horizontal reactor. The reactor has an outer shell to contain the reaction mixture; a circulation tube to establish an internal flow path in the reactor; an impeller for mixing; and heat exchange means for addition or removal of heat of a reaction carried out within the reactor.

The reactor as disclosed herein has a conventional flow pattern. That is, fluids enter the reactor before the impeller through suitable nozzles. After mixing in the impeller, the mixed fluids flow through an annular space outside of the circulation tube and the outer shell through a reversal zone in which direction of fluid flow reverses in the end of the shell at the hydraulic head. Flow then proceeds through an annular passage between the circulation tube and the outer shell, thereafter through a second reversal zone in which direction of fluid flow reverses in the end of the shell opposite the hydraulic head. Fluid then flows back to the impeller within the circulation tube and in contact with the heat exchange means.

A continuous mixing reactor of the present disclosure has an outer shell having interior and exterior walls. The shell has one or more inlets to allow introduction of fluids into the reactor. The shell has a hydraulic head that forms and closes one end of the shell. The hydraulic head has a shaft sealing means and any required bearings for the impeller shaft. The head incorporates a reversal zone for flow of liquids from the impeller as described and illustrated herein.

At the end of the shell opposite the hydraulic head is a heat exchange medium header. This header provides for flow of coolant into and out of the heat exchange means described further below.

The shell has a generally cylindrical portion (cylinder) between the between the hydraulic head and the heat exchange medium header. The cylindrical portion has a central section and two opposite end sections. The central section of the cylindrical portion is a tube having substantially the same diameter along the length of the tube. Each end of the cylindrical portion is a conical section, that is, has a progressively decreasing diameter in a direction away from the central section of the cylinder. That is, the cylindrical portion has a tube of uniform diameter through the center of the reactor shell, and this tube tapers at both end sections as the cylindrical portion approaches the hydraulic head and the heat exchange medium header, at the respective ends. The tapering may be uniform (concentric conical end section) or non-uniform (eccentric conical end section). For example, a non-uniform tapering occurs when the bottom of the reactor fails to slope upward at the same angle as the top of the reactor slopes downward, such as remains flat. (See FIG. 1.)

In one embodiment, the conical end section near the hydraulic head is concentric. In one embodiment, the conical end section near the heat exchange medium header is concentric. In one embodiment at least one of the conical end sections is eccentric. In one embodiment both end sections are concentric. In one embodiment the end section near the hydraulic head is eccentric.

The shell also has a discharge outlet to allow for removal of material from the continuous mixing reactor. The discharge outlet is located on a surface of the central section of the cylindrical portion of the outer shell. The discharge outlet may be located on an upper (top) surface of the shell or on a lower (bottom) surface of the shell. The discharge outlet may be upstream of the conical end section near the heat exchange medium header. In one embodiment, product is removed from a discharge outlet located on the top surface of the reactor.

The continuous mixing reactor disclosed herein has a hollow, open-ended circulation tube positioned axially or concentrically within the shell and spaced from the interior wall of the shell, forming an annular passage therewith. The circulation tube is generally congruent with the outer shell, such as with the cylindrical portion of the shell. One end of the circulation tube is near the hydraulic head of the shell. At this end, the circulation tube may taper to maintain the annular passage through the conical section of the cylinder approaching the hydraulic head. The opposite end, referred to herein as the terminal end of the circulation tube (away from the hydraulic head and nearer to the heat exchange medium header) terminates at or downstream from (based on direction of flow of fluid through the impeller through a reversal area in the hydraulic head then through the annular passage between the shell and the circulation tube) a tangential plane extending through the shell at the intersection of the central section and the conical end section of the cylindrical portion of shell.

The continuous mixing reactor has an impeller received within the end of the circulation tube nearer to the hydraulic head. The impeller provides for mixing and creating a cyclic flow of fluids through the tube and in the annular passage surrounding said tube. The impeller is mounted on a shaft which rotates within in the hydraulic head. The hydraulic head forms the end of the shell adjacent to the impeller and contains shaft sealing means, such as suitable packing glands and any required bearings for the impeller shaft. The impeller is driven by a suitable prime mover, such as a driving motor, turbine or engine.

Figure 2:
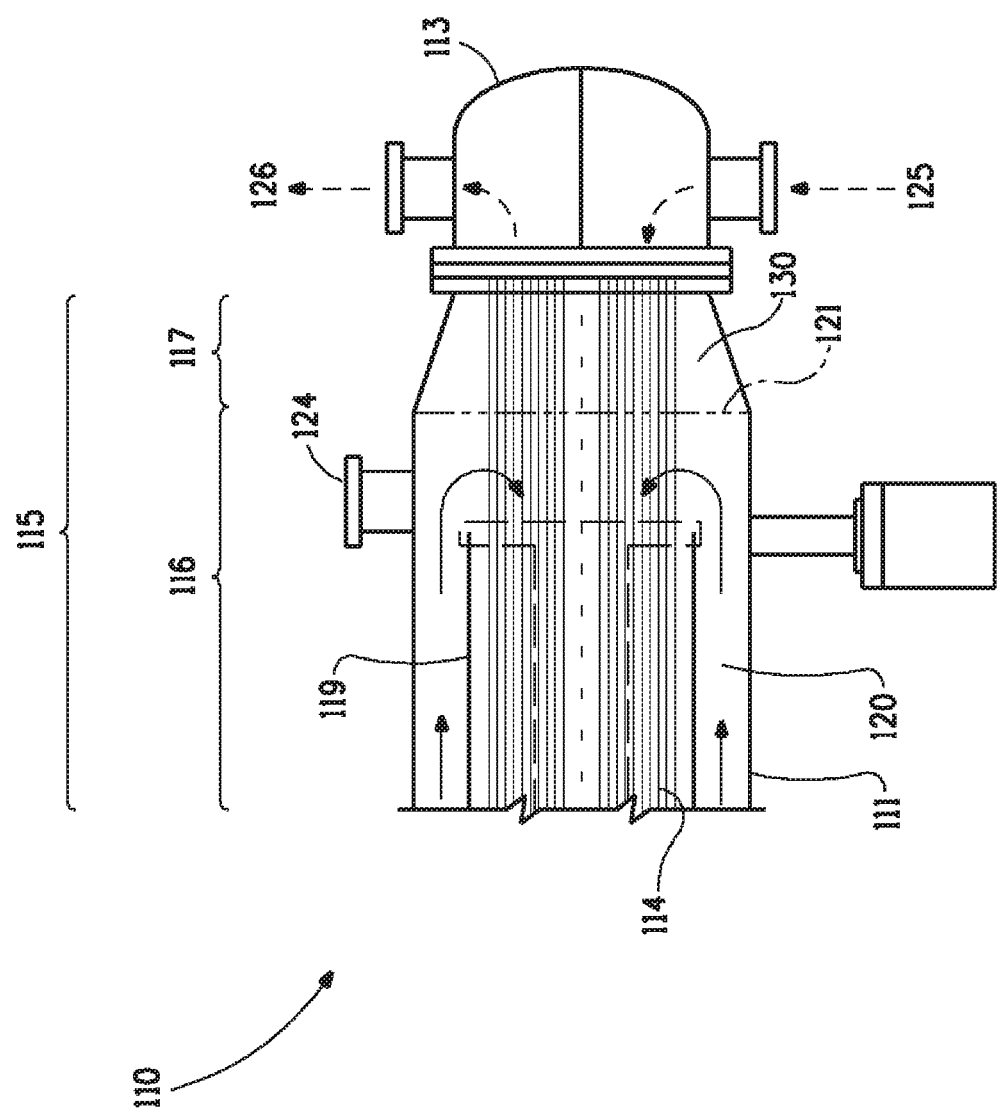
FIG. 2 is a view of the reactor of FIG. 1 showing a section of the reactor that includes the heat exchange medium header and flow of liquid.
Figure 3:
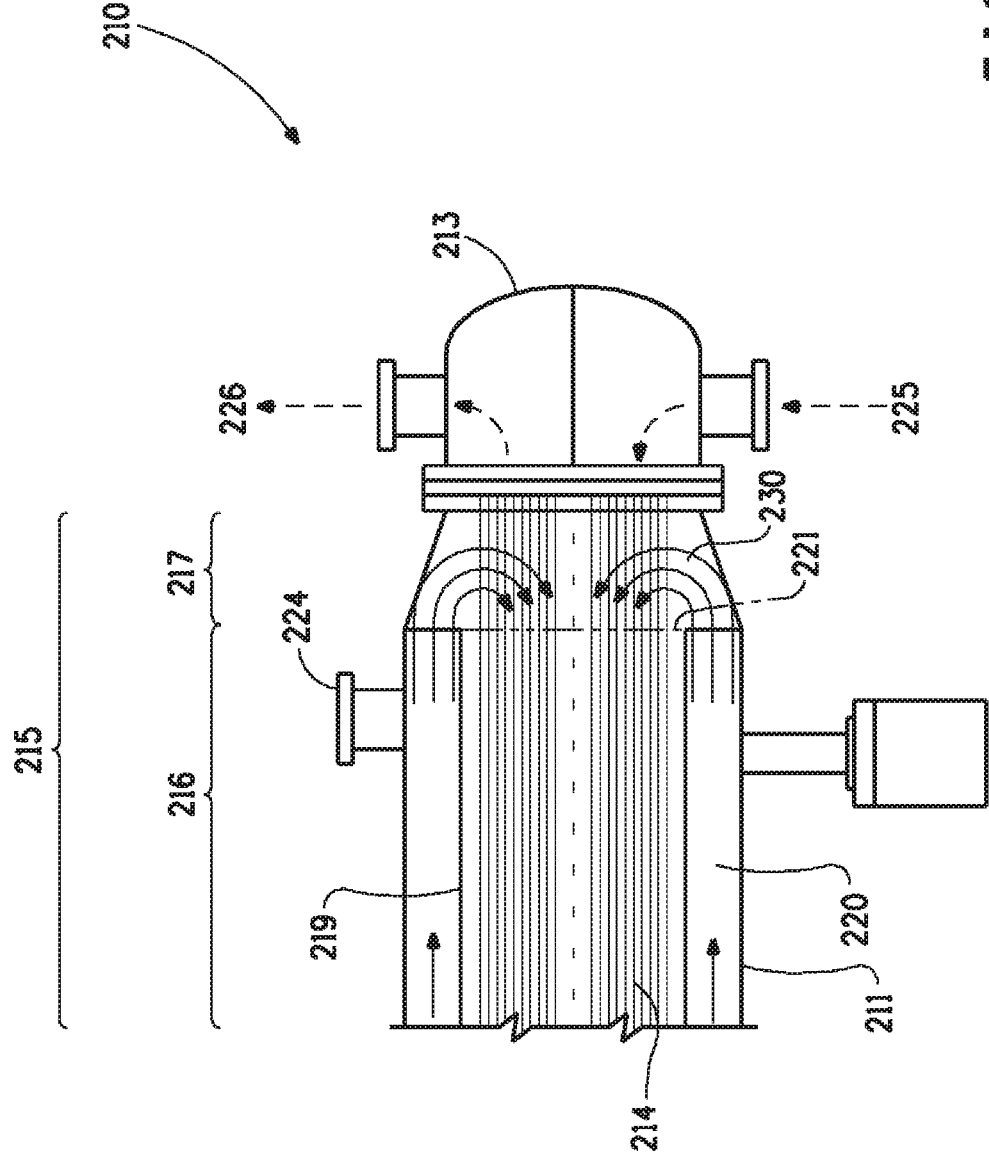
FIG. 3 is a cross-section view of a continuous mixing reactor as disclosed herein showing a section of the reactor that includes the heat exchange medium header and flow of liquid.

The continuous mixing reactor has heat exchange means, which penetrates the outer shell at the end of the shell opposite the impeller and extends from a tube sheet into the open end of the circulation tube opposite of the impeller. The heat exchange means extends through the heat exchange medium header of the outer shell into the circulation tube substantially the length of the central portion of the cylindrical portion of the outer shell. The heat exchange means as disclosed herein can have an elongated U-section heat exchanging tube bundle. Individual tubes of the tube bundle are rolled into or otherwise attached to a tube sheet, which closes in the heat exchange medium header. Tube bundles are illustrated in FIGS. 1-3 herein. An alternative form of heat exchanger is disclosed in U.S. Pat. No. 2,800,307. A typical heat exchange medium header having a central wall or partition therewithin dividing the tube ends from one another permits distribution of heating or cooling medium (coolant) to the tubes of the bundle.

Nozzles and/or feed lines are provided for feeding fluid, such as individual fluid components or blended fluids or mixtures to be circulated into the continuous mixing reactor. The nozzles and/or feed lines extend both through the outer shell and inner circulation tube upstream of flow into the impeller. The feeds and reaction mixture are discharged into the circulation tube upstream of the impeller. The impeller is thus arranged for taking suction from the circulation tube and discharging fluid into the hydraulic head. Within the latter, the flow of fluid is reversed in a reversal zone and flow is directed into the annular passage between the outer shell and circulation tube.

In a conventional continuous mixing reactor, the circulation tube extends from the impeller end toward the heat exchange medium header of the reactor. The terminal end of the circulation tube in a conventional reactor terminates within the central section of the cylindrical portion of the outer shell, as referred to herein as a "non-extended" circulation tube. As shown in FIG. 2, there is created an annular region defined by the outer shell, the heat exchange means and the tube that is a stagnant area downstream of the circulation tube near the tube sheet. Neither fluid flow nor heat exchange is efficient in the annular region.

In the present disclosure, the circulation tube terminates at or downstream of (based on direction of flow through the annular passage) a tangential plane extending through the shell at the intersection of the central section and the conical end section of the cylindrical portion of the outer shell, and is referred to herein as an "extended circulation tube"— extended relative to the non-extended circulation tube in a conventional reactor. The size of the annular region as defined by the outer shell, the heat exchange means and the tangential plan at the terminal end of the circulation tube is reduced relative to the size of this region in a conventional reactor. Fluid flow and heat exchange are improved.

In one embodiment, the terminal end of the circulation tube terminates at a tangential plane extending through the shell at the intersection of the central section and the conical end section of the cylindrical portion of shell. In one embodiment, the terminal end of the circulation tube terminates downstream from a tangential plane extending through the shell at the intersection of the central section and the conical end section of the cylindrical portion of shell. In one embodiment, the discharge outlet is located on an upper surface of the shell at or upstream of the intersection of the central section and conical end section of the cylindrical portion of the shell nearer to the heat exchange medium header. In one embodiment, the terminal end of the circulation tube terminates in an open end in advance of, upstream of the tube sheet.

In one embodiment of the disclosure, the reactor has a flow distribution plate attached to the terminal end of the circulation tube. The flow distribution plate may be perforated. The flow distribution plate allows fluid to pass from the circulation tube into the annular region where reversal of fluid flow occurs.

In one embodiment of the disclosure, the terminal end of the circulation tube is located at a position at or downstream of (based on direction of flow through the annular passage) a tangential plane at the intersection of the central section and conical end section of the cylindrical portion of the outer shell nearer to the heat exchange medium header, and within the terminal end of the circulation tube is provided a flow distribution plate. Thus, in one embodiment, the circulation tube is an extended circulation tube having a flow distribution plate.

The continuous mixing reactor disclosed herein provides certain advantages when used in an alkylation process. When the reactor disclosed herein is used in an alkylation process, advantages include better management of reaction temperature, more efficient use of heat transfer surface, decreased tube wear, better flow distribution to the center of the tube bundle, reduced size of annular region (as defined herein), which corresponds to less stagnant area for side reactions to occur.

The continuous mixing reactor as disclosed herein is suitable processes having (1) a relatively large quantity of heat of reaction, as well as (2) a relatively large reaction time (residence time) requirement as may be desired, for example in an alkylation process.

One embodiment of the disclosure is an alkylation process. An alkylation process comprises contacting at least one olefin with at least one isoparaffin (reactant isoparaffin) in the presence of an acid catalyst to produce a product comprising isoparaffins (product isoparaffins) wherein the contacting is performed in a reactor as described herein. One or more olefins can be used. One or more reactant isoparaffins can be used to react with the olefin. The product isoparaffins have longer carbon chains than the reactant isoparaffins.

The olefin is a light olefin, generally a $C_3$ to $C_5$ olefin, such as isobutylene. One or more $C_3$ to $C_5$ olefins may be used. The reactant isoparaffin is generally a mixture of isoparaffins, for example, a mixture of isoparaffins comprising isoparaffins having 5 to 16 carbon atoms.

Alkylation processes are catalyzed by acid. Any acid catalysts, homogeneous or heterogeneous, can be used in the invention. Examples of suitable acid catalysts include, but are not limited to, sulfuric acid, hydrogen fluoride, acidic ion exchange resin, zeolite, fluorosulfonic acid, boron trifluoride, antimony pentafluoride, phosphoric acid, metal halide such as aluminum chloride and aluminum bromide, complex of aluminum chloride and sulfuric acid, solid acid catalyst, and combinations of two or more thereof. The catalyst can be sulfuric acid for it is readily available and effective in alkylation.

Acid strength of the catalyst is preferably maintained to provide sufficient catalytic activity. For example, the useful range for sulfuric acid can be generally in the range of about 86 to 99 weight percent.

The volume ratio of catalyst to total hydrocarbon (olefin and reactant isoparaffins) can be generally in the range of from about 0.001:1 to about 100:1, or about 0.1:1 to about 10:1, and or about 0.5:1 to about 10:1. Normal operation of a reactor as disclosed herein for sulfuric acid-catalyzed alkylation service uses a target acid to hydrocarbon ratio of 1:1. Ratio of acid to hydrocarbon may not range above 1.5:1, thus the volume ratio of catalyst to total hydrocarbon can be 1:1 to 1.5:1.

The contacting of the olefin with the reactant isoparaffin can be carried out under conditions sufficient to alkylate the olefin(s). Such conditions can include a temperature in the range of from about −40° C. to about 260° C., such as about −15° C. to about 95° C., or about 0° C. to about 55° C. under a pressure that can accommodate the temperature range such as, for example, about atmospheric to about 35 MPa, or in the range of about 65 to about 7000 kPa, or in the range of about 300 to about 1750 kPa for a period of from about 1 second to about 100 minutes, or in the range of about 0.1 to about 30 minutes, or in the range of about 1 minute to about 20 minutes. In one embodiment, temperature is in the range of about 4° C. to about 20° C. In one embodiment, pressure is in the range of about 340 to about 500 kPa.

The contacting is carried out in the continuous mixing reactor as disclosed herein.

DETAILED DESCRIPTION OF THE FIGURES

FIG. 1 is a cross-section view of a continuous mixing reactor 10 of the prior art, illustrating elements of the reactor disclosed herein. Reactor 10 has reactor shell 11, hydraulic head 12 forming one end of the shell and heat exchange medium header 13 forming the opposite end of shell 11. Reactor 10 has an elongated U-section heat exchanging tube bundle 14 which terminates in heat exchange medium header 13.

FIG. 1 also illustrates reactor 10 outer shell 11 having a generally cylindrical portion 15 between hydraulic head 12 and heat exchange medium header 13, which tapers prior to each end. As illustrated, generally cylindrical portion 15 of outer shell 11 has a central section 16 having a substantially uniform diameter that tapers into a concentric conical section 17 at heat exchange medium header 13 and into an eccentric conical section 18 at hydraulic head 12 at the opposite end of shell 11. As will be appreciated by those skilled in the art, the conical sections may taper into either concentric conical sections or eccentric conical sections.

Circulation tube 19 is received within shell 11, with one open end positioned within hydraulic head 12 and one open end opposite hydraulic head 12 (nearer to heat exchange medium header 13) positioned such that circulation tube 19 terminates upstream of (based on direction of flow of fluid through the annular passage 20 between shell 11 and circulation tube 19) a tangential plane 21 extending through shell 11 at the intersection of central section 16 and the conical section 17 of cylindrical portion 15 of shell 11. Impeller 22 is positioned in open end of circulation tube 19 within hydraulic head 12. Motor 23 drives impeller 22. The end of circulation tube 19 opposite impeller 22 is also open to permit fluid flow from annular passage through tube bundle 14.

FIG. 1 is illustrative of an alkylation process in which Acid (sulfuric acid) and HC (hydrocarbon) are fed to reactor 10 through inlets to circulation tube 19 upstream of impeller 22. Fluid flows through impeller 22 into annular passage 20 between shell 11 and circulation tube 19 with flow around open end of circulation tube 19 nearest heat exchange medium header 13 and through tube bundle 14. Flow through reactor 1 is illustrated by arrows.

Product emulsion exits reactor 10 at outlet 24 to an emulsion settler (not shown). Also, FIG. 1 designates coolant inlet 25 and outlet 26 of tube bundle assembly 14 in the heat exchange medium header 13.

FIG. 2 is an expanded view of the continuous mixing reactor of FIG. 1 showing a portion of reactor 110 that includes heat exchange medium header 113. Solid arrows illustrate flow of fluid through annular passage 120 between circulation tube 119 and shell 111 around open ends of circulation tube 119 and through tube bundle 114. Dashed arrows illustrate flow of coolant through inlet 125 into heat exchange medium header 113 to tube bundle 114 and from tube bundle 114 through outlet 126 of heat exchange medium header 113. Circulation tube 119 extends toward heat exchange medium header 113 terminating upstream of a tangential plane 121 extending through shell 111 at the intersection of central section 116 and conical section 117 of cylindrical portion 115 of shell 111. Annular region 130 shows an area of the reactor 110 where tube bundle 114 cooling is under-utilized for lack of material flow. Outlet 124 is provided for product to exit reactor 110.

FIG. 3 is an expanded view of a continuous mixing reactor as disclosed herein showing a portion of reactor 210 that includes heat exchange medium header 213. Solid arrows illustrate flow of fluid through annular passage 220 between circulation tube 219 and shell 211 around open ends of circulation tube 219 and through tube bundle 214. Dashed arrows illustrate flow of coolant through inlet 225 into heat exchange medium header 213 to tube bundle 214 and from tube bundle 214 through outlet 226 of heat exchange medium header 213. Circulation tube 219 extends toward heat exchange medium header 213 terminating at a tangential plane 221 extending through shell 111 at the intersection of the central section 216 and conical section 217 of cylindrical portion 215 of shell 211. Annular region 230 shows an area of reactor 210 where greater utilization of cooling capacity of tube bundle 214 is achieve relative to FIG. 2. Outlet 224 is provided for product to exit reactor 210.

EXAMPLES

Example 1 and Comparative Example A

Flow distribution such as may occur in alkylation processes were simulated based on reactors as shown in FIGS. 2 and 3 and analyzed using CFD modeling in Comparative Example A (an embodiment of a reactor of the prior art) and Example 1 (an embodiment using a reactor as disclosed herein), respectively, using ANSYS Fluent CFD Software (ANSYS, Inc., 275 Technology Drive, Canonsburg, Pa. 15317). The same conditions were used for simulations in reactors of FIG. 2 and FIG. 3.

The CFD results showed the improvement in flow distribution for the reactor as disclosed herein into stagnant regions near the tube sheet of the heat transfer medium, better flow distribution at the end of the circulation tube (that is, flow not all turning at the end of circulation tube), and better flow distribution within the tube bundle, relative to flow in reactor of the prior art.

Example 2 and Comparative Example B

Alkylation processes were performed using the reactors as shown in FIG. 2 (Comparative Example B, an embodiment using a reactor and process of the prior art) and FIG. 3 (Example 2, an embodiment using a reactor and process as disclosed herein). The same process conditions were used for an alkylation process using sulfuric acid as catalyst and $C_3$ to $C_5$ olefin and a mixture of $C_5$ to $C_{16}$ isoparaffins. The target acid to hydrocarbon ratio was 1:1. The temperature was 4° C. to 20° C. (about 40° F. to 65° F.) and the pressure was and 340 to 490 kPa (about 50 to 70 psig).
Results found multiple benefits for using the reactor and process of Example 2 relative to Comparative Example B. The benefits include:
  10-12% increase in heat transfer values.
  Approximately 3° F. (2.5° F. to 3.5° F. or 1.3 to 1.9° C.) reaction temperature drop at a constant olefin flow rate or 9 to 12% olefin flow rate increase at constant reaction temperature.
Other benefits will of the reactor and process will be appreciated by those skilled in the art.

What is claimed is:

1. A continuous mixing reactor having (a) an outer shell, wherein the outer shell has an interior wall and an exterior wall; one or more inlets for fluids, a hydraulic head (or circulating head) forming one end of the shell, a heat exchange medium header at the opposite end of the shell from the hydraulic head; wherein the shell has a generally cylindrical portion between the hydraulic head and the heat exchange medium header, having a central section and two opposite end sections, the central section having a substantially uniform diameter and each end section is a conical section, and a discharge outlet positioned on a surface of the cylindrical portion; and (b) a hollow circulation tube, open at both ends, extending from the hydraulic head to a terminal end opposite of the hydraulic head and nearer to the heat exchange medium header, and positioned axially within the shell and spaced from the interior wall thereof such that an annular passage is formed between the circulation tube and the shell; and (c) an impeller received within and positioned adjacent to the end of the circulation tube within the hydraulic head of the shell, wherein the impeller provides for mixing of fluid within the reactor, creating a cyclic flow of fluids through said tube; and (d) heat exchange means penetrating the outer shell, wherein the heat exchange means extends from the heat exchange medium header into the open end of the circulation tube opposite of the impeller, wherein the heat exchange means penetrates substantially the length of the central section of the cylindrical portion of the outer shell; characterized as having the end of the circulation tube nearer to the heat exchange medium header terminates at or downstream from a tangential plane extending through the shell at the intersection of the central section and the conical end section of the cylindrical portion of shell.

2. The reactor of claim 1 having the end of the circulation tube nearer to the heat exchange medium header terminate at a tangential plane extending through the shell at the intersection of the central section and the conical end section of the cylindrical portion of shell.

3. The reactor of claim 1 having the end of the circulation tube nearer to the heat exchange medium header terminate downstream from a tangential plane extending through the shell at the intersection of the central section and the conical end section of the cylindrical portion of shell.

4. The reactor of claim 1 wherein the conical end section near the hydraulic head is concentric.

5. The reactor of claim 1 wherein the conical end section near the heat exchange medium header is concentric.

6. The reactor of claim 1 wherein at least one of the conical end sections is eccentric.

7. The reactor of claim 1 wherein both end sections are concentric.

8. The reactor of claim 1 wherein the end section near the hydraulic head is eccentric.

9. The reactor of claim 2 having nozzles for feeding fluid into through the outer shell and circulation tube upstream of flow into the impeller.

10. The reactor of claim 3 having nozzles for feeding fluid into through the outer shell and circulation tube upstream of flow into the impeller.

11. The reactor of claim 2 having an annular region defined by the outer shell, the heat exchange means and the tangential plane at the terminal end of the circulation tube.

12. The reactor of claim 3 having an annular region defined by the outer shell, the heat exchange means and the tangential plane at the terminal end of the circulation tube.

13. An alkylation process comprising contacting an olefin with an isoparaffin in the presence of an acid catalyst to produce a product comprising isoparaffins wherein the contacting is performed in a reactor as set forth in claim 1.

14. An alkylation process of claim 13 wherein the olefin is one or more $C_3$ to $C_5$ olefin and the isoparaffin is a mixture of isoparaffins.

15. An alkylation process of claim 13 wherein the acid catalyst is sulfuric acid, hydrogen fluoride, acidic ion exchange resin, zeolite, fluorosulfonic acid, boron trifluoride, antimony pentafluoride, phosphoric acid, metal halide such as aluminum chloride and aluminum bromide, complex of aluminum chloride and sulfuric acid, solid acid catalyst, or a combination of two or more thereof.

16. An alkylation process of claim 15 wherein the acid is sulfuric acid.

17. An alkylation process of claim 16 having conditions of a temperature in the range of from about −40° C. to about 260° C. and a pressure in the range of about atmospheric to about 35 MPa and a volume ratio of catalyst to total hydrocarbon in the range of from about 0.001:1 to about 100:1.

18. An alkylation process of claim 16 having conditions of a temperature in the range of from about −15° C. to about 95° C. and a pressure in the range of about 65 to about 7000 kPa and a volume ratio of catalyst to total hydrocarbon in the range of from about 0.1:1 to about 10:1.

19. An alkylation process of claim 16 having conditions of a temperature in the range of from about 4° C. to about 20° C. and a pressure in the range of about 340 to about 500 kPa and a volume ratio of catalyst to total hydrocarbon (olefin and reactant isoparaffins) in the range of from about 1:1 to about 1.5:1.

* * * * *